(12) United States Patent
Mayeaux

(10) Patent No.: US 7,875,109 B1
(45) Date of Patent: Jan. 25, 2011

(54) INTEGRAL FLOW RESTRICTOR VALVE

(75) Inventor: Donald P. Mayeaux, St. Amant, LA (US)

(73) Assignee: A+ Manufacturing, LLC, Gonzales, LA (US)

( * ) Notice: Subject to any disclaimer, the term of this patent is extended or adjusted under 35 U.S.C. 154(b) by 328 days.

(21) Appl. No.: 12/044,543

(22) Filed: Mar. 7, 2008

Related U.S. Application Data

(60) Provisional application No. 60/893,860, filed on Mar. 8, 2007.

(51) Int. Cl.
*B01D 49/00* (2006.01)

(52) U.S. Cl. .................... 96/413; 138/45; 251/121; 251/127; 73/864.91; 73/864.83; 73/863

(58) Field of Classification Search .......... 96/413; 138/45; 251/121, 127; 73/864.91, 864.83, 73/863
See application file for complete search history.

(56) References Cited

U.S. PATENT DOCUMENTS

| | | | | |
|---|---|---|---|---|
| 5,147,426 A | * | 9/1992 | Koike et al. | 73/863.22 |
| 5,237,881 A | * | 8/1993 | Ross | 73/863.12 |
| 5,627,328 A | * | 5/1997 | Sheridan et al. | 73/863.83 |
| 5,741,960 A | * | 4/1998 | Payne et al. | 73/23.41 |
| 6,241,950 B1 | * | 6/2001 | Veelenturf et al. | 422/103 |
| 6,418,802 B1 | * | 7/2002 | Wood | 73/865.5 |
| 6,539,968 B1 | * | 4/2003 | White et al. | 137/10 |
| 7,232,477 B2 | * | 6/2007 | Rodgers | 96/413 |
| 7,257,987 B2 | * | 8/2007 | O'Brien et al. | 73/23.41 |
| 7,431,045 B2 | * | 10/2008 | Mudd et al. | 137/487.5 |
| 2003/0079523 A1 | * | 5/2003 | Lechner-Fish | 73/23.41 |
| 2004/0094203 A1 | * | 5/2004 | Nimberger | 137/327 |
| 2005/0045239 A1 | * | 3/2005 | Krieger et al. | 138/44 |
| 2005/0075711 A1 | * | 4/2005 | Neary | 623/1.11 |
| 2008/0041471 A1 | * | 2/2008 | Paterson et al. | 137/625.47 |

* cited by examiner

*Primary Examiner*—Jason M Greene
*Assistant Examiner*—Dung Bui
(74) *Attorney, Agent, or Firm*—Joseph T Regard Ltd plc

(57) ABSTRACT

A gas sample cylinder outlet valve having a flow restricting element associated therewith. The preferred embodiment of the flow restricting element comprises an orifice constructed of a low thermal conduction material such as a plastic. Preferably the outlet valve $C_v$ characteristic is large relative to the orifice $C_v$ characteristic resulting in essentially all of the gas pressure drop taking place across said orifice and therefore essentially all of the J-T effect cooling taking place at said orifice. Due to the low thermal conductivity construction of said orifice an insignificant amount of cooling takes place upstream of the valve mechanism. Test have shown that the integral orifice outlet valve having a large $C_v$ characteristic is more efficient then the typical sample cylinder outlet valve and extension tube and/or flow restrictor combination.

27 Claims, 5 Drawing Sheets

INTEGRAL FLOW RESTRICTOR VALVE

PRIORITY CLAIM

This application claims the benefit of Provisional Application Serial Number 60893860 filed Mar. 8, 2007 entitled SAMPLE CYLINDER WITH VALVE listing as inventor Donald P. Mayeaux.

TECHNICAL FIELD OF INVENTION

The present invention relates to the spot sampling of natural gas. The preferred embodiment of the present invention contemplates a flow restrictor with integral thermal isolation which is more compact and user friendly then current flow restriction means.

GENERAL BACKGROUND OF THE INVENTION

Natural Gas is a vital source of heat energy in the United States. Its selling price is based on volume and heat content. The heat content is greatly influenced by the presence of the heavy (higher molecular weight) components. These heavy components also have a large influence on the gases physical properties, which in turn impact flow rate and volume calculations. The heat content and physical properties of natural gas are primarily determined by calculations based on gas composition.

A common means for determining the gas composition of a Natural gas source consist of capturing a spot sample of the source gas, such, for example, in a pressurized pipeline, transferring the gas sample to a storage vessel where the sample can be stored, then transporting the storage vessel, such as a sample cylinder, to a laboratory wherein it is analyzed by Gas Chromatography.

The constant volume type of sample cylinders, such as the SWAGELOK™ part # 316L-HDFA-300, require purging with sample gas to remove residual contaminates (such as air) prior to filling with sample gas. Most filling techniques require a flow restrictor, which is thermally isolated from the sample cylinder.

The Gas Processors Association (GPA) standard 2166 "obtaining Natural Gas Sample for analysis by Gas Chromatography" requires the use of an extension tube (pigtail) of at least 36 inches in length downstream of the sample cylinder outlet valve. Refer to FIG. 1.

A valve and/or restriction is connected to the end of the extension tube. Said 36" length of tubing is designed to provide thermal isolation between said valve and/or flow restrictor and the outlet valve of the sample cylinder. Said thermal isolation is required for cylinder purging methods which require rapid depressurization of the sample cylinder gas. Otherwise, when the cylinder is purged with the source gas, the resulting Joule-Thomson (J-T) effect may cause the cylinder outlet valve to cool below the Hydrocarbon Dewpoint temperature (HDPT) of said source gas.

The resulting condensation of the heavier sample gas components render the remaining sample gas unrepresentative of the original gas source. This in turn impacts the calculated heat value, volume, and monetary value of the source gas. When utilizing the extension tube with a valve and/or restrictor the bulk, but not all, of the J-T effect cooling takes place at the outlet end of said extension tube. However, some pressure drop takes place across the outlet valve and depending on its $C_v$ characteristics, causes cooling of the outlet valve.

The pigtail type of thermal isolation is awkward and must be installed and removed from the sample cylinder each time that a spot sample is taken. It is therefore rarely used by the measurement technician for spot sampling. This has been a great source of concern since improper sampling can have a significant impact on assessment of the monetary value of Natural gas.

GENERAL DISCUSSION OF THE INVENTION

Unlike prior art, the present invention provides a means for thermal isolation between the outlet valve body and the J-T effect cooled gases during depressurization of the sample cylinder.

The preferred embodiment of the present invention contemplates a gas sample cylinder outlet valve having a flow restricting orifice integrated in the valve body downstream of the valving mechanism. Refer to FIG. 2. The orifice is constructed of a low thermal conduction material such as a plastic. Preferably the outlet valve $C_v$ characteristic is large relative to the orifice $C_v$ characteristic resulting in essentially all of the gas pressure drop taking place across said orifice and therefore essentially all of the J-T effect cooling taking place at said orifice. Due to the low thermal conductivity construction of said orifice an insignificant amount of cooling takes place upstream of the valve mechanism. Test have shown that the integral orifice outlet valve having a large $C_v$ characteristic is more efficient then the typical sample cylinder outlet valve and extension tube and/or flow restrictor combination. Refer to FIG. 3. Test results may be found in my earlier provisional patent application Serial Number 60893860 filed Mar. 8, 2007 entitled "Sample Cylinder with Valve", the contents of which are incorporated herein by reference thereto.

Lastly it is an object of the present invention to provide a means for conforming to the industry standards which govern the methods for spot sampling of natural gas with a constant volume sample cylinder.

DETAILED DISCUSSION OF THE INVENTION

Figure 1:
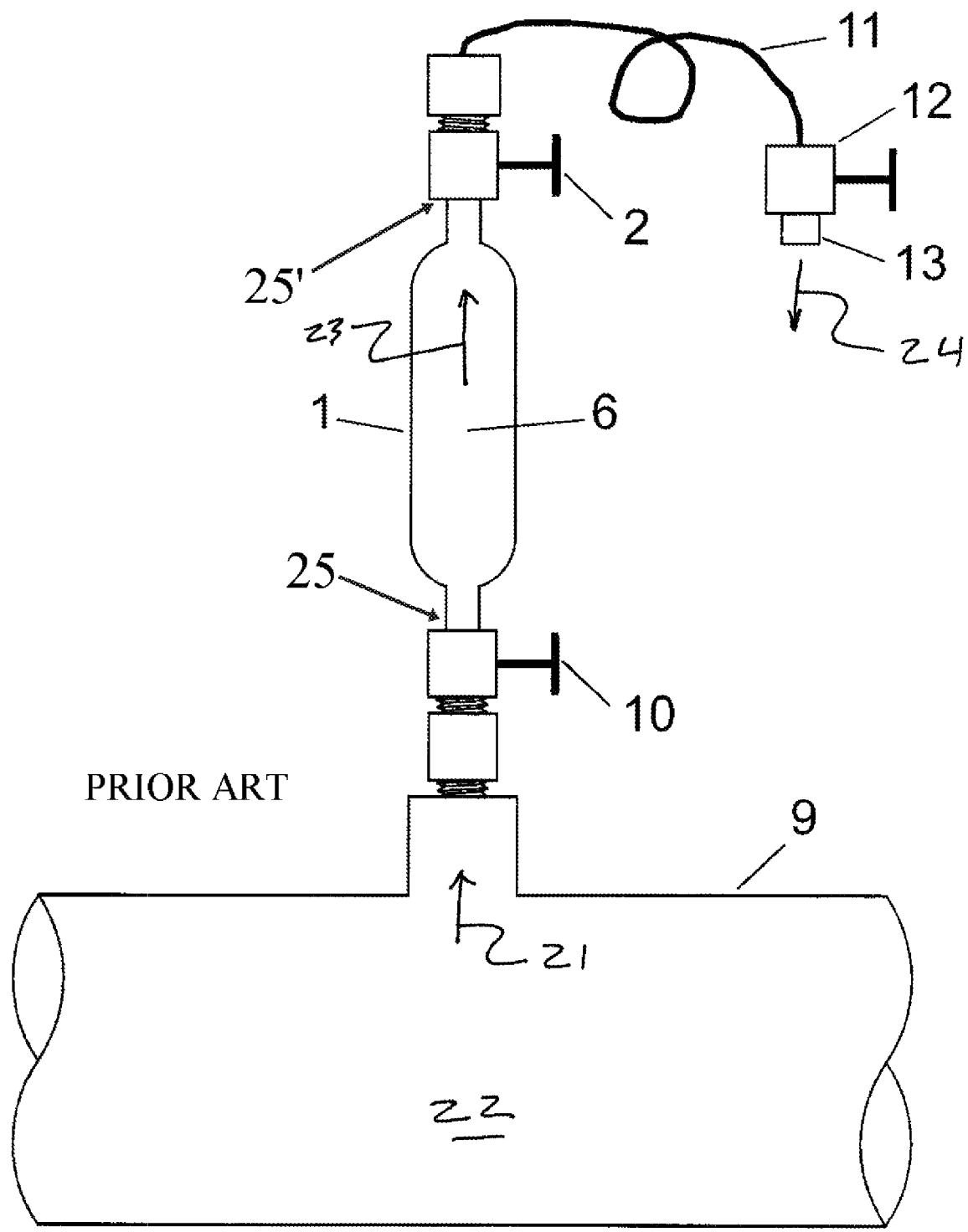
FIG. 1 is a schematic view of the Gas Processors Association (GPA) extension tube (pigtail) with valve and/or flow restrictor.
Figure 2:
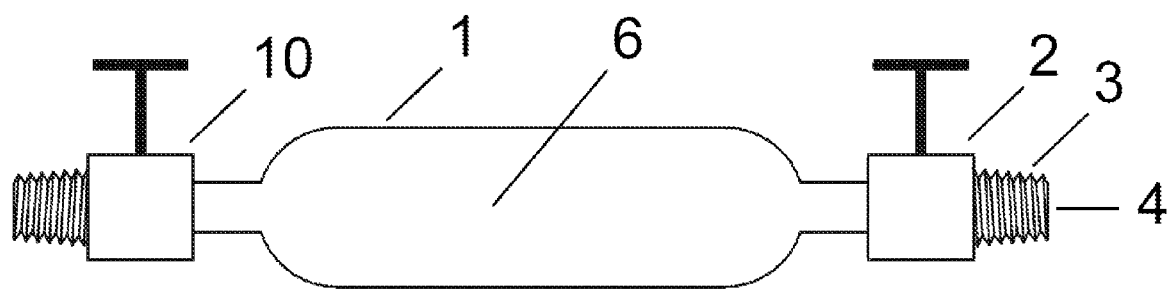
FIG. 2 is a schematic view of a gas sample cylinder with an outlet valve having an integral flow restrictor orifice of the present invention.

Referring to FIG. 1, the prior art requires the purging of a sample cylinder 1 having first 25 and second ends 25' (which may be threaded as shown in FIG. 2), the first end engaging gas 22 from a source such as pipeline 9. To execute the purging step, GPA standard 2166 requires the opening of inlet valve 10 to admit 21 source gas 22 from pipeline 9 to fill inlet cavity 6 of gas sample cylinder 1, where it passes through 23 the interior of cylinder 1 and out of the cylinder via opened outlet valve 2, into the first end of an extension tube (pigtail) 11, then out of the second end of the tube through extension tube valve 12 to a low pressure location, typically comprising the local atmosphere.

In some cases a flow reducing orifice 13 is attached to extension tube valve 12 where the gas passes therethrough 24 in the above operation. In such cases wherein a flow reducing orifice 13 is utilized, extension tube valve 12 is usually either in the fully opened state during the purging cycle, or completely eliminated.

Figure 3:
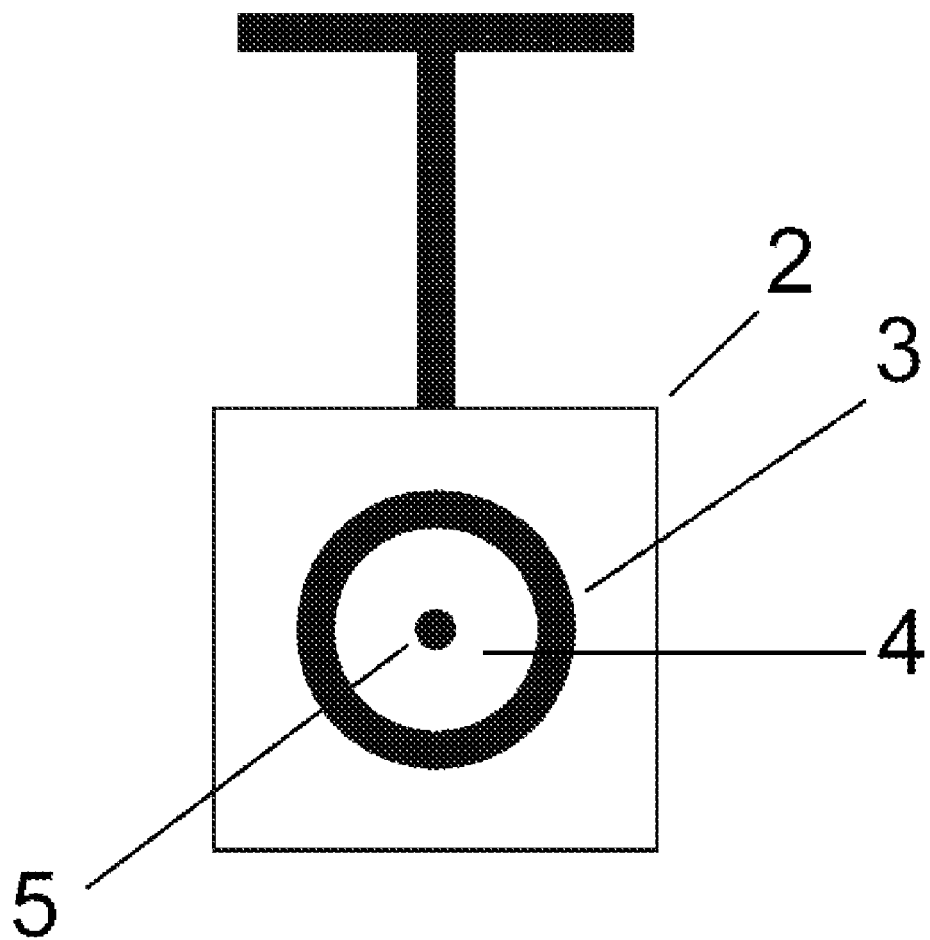
FIG. 3 is a schematic end view of the outlet valve of FIG. 2 showing the valve outlet port, flow restrictor assembly, and flow restrictor orifice.
Figure 4:
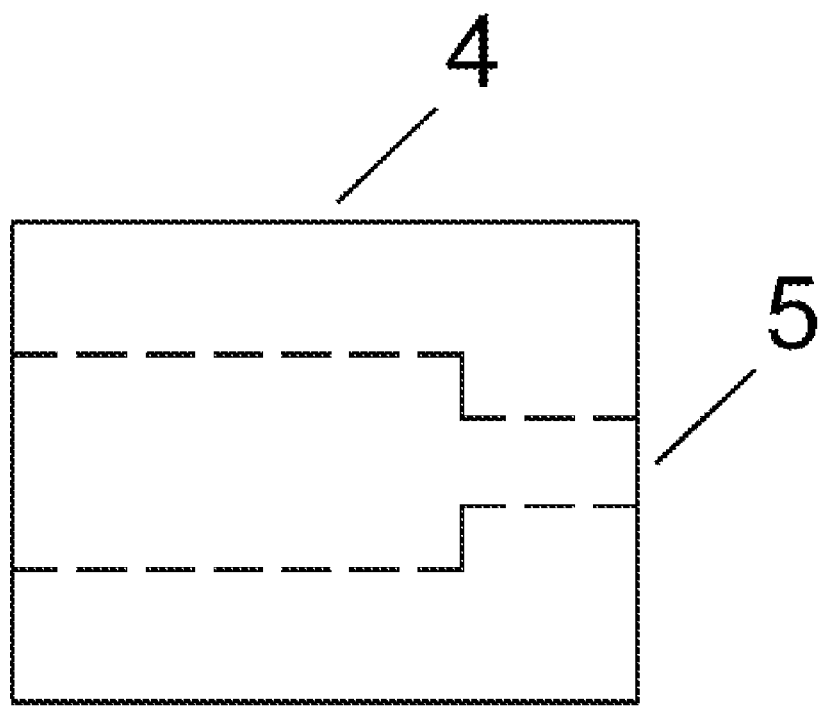
FIG. 4 is a schematic side view of flow restrictor assembly 4 shown in FIG. 2, revealing flow restricting orifices.
Figure 5:
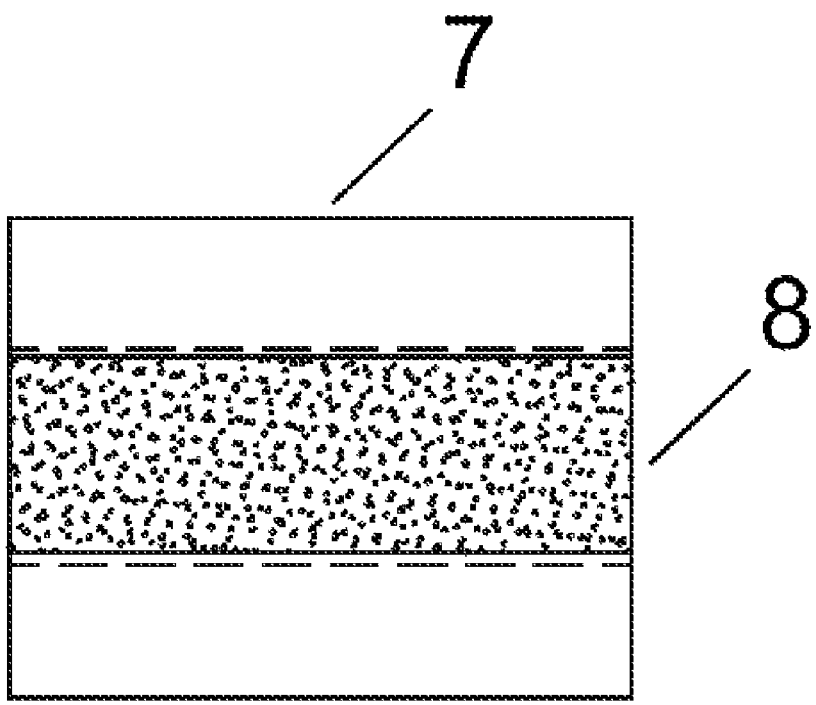
FIG. 5 is a schematic side view of an alternate flow restrictor assembly 7 of the present invention, revealing sintered flow restrictor 8.

Referring to FIGS. 2 through 4, the present invention utilizes a outlet valve 2 having a flow restrictor assembly 4 having an orifice 5 engaging the gas sample cylinder 1. Said flow restrictor assembly 4 is integrated into said outlet valve 2 outlet port 3 and is preferably formed of a material having low thermal conductivity characteristics such as, for example, polymeric material e.g., NYLON, TEFLON (for example, PTFE or PCTFE), or plastic, for reasons further discussed below.

There are GPA standard 2166 spot sampling methods which require purging of gas sample cylinder 6 with sample gas, prior to a final filling step in which sample gas is captured in internal cavity 6. A typical purging cycle during execution of a typical GPA Standard 2166 spot sampling method requires venting gas contained in gas sample cylinder 1 through outlet valve 2.

By opening outlet valve 2 during a said purging cycle, gas contained in the gas sample cylinder 1 can be vented to an external low pressure location, typically the local atmosphere. In flowing from the internal cavity 6 of gas sample cylinder 1 to said external location, said gas flows through the internal valving mechanism of outlet valve 2, then flowing through orifice 5 of flow restrictor orifice assembly 4. In the preferred embodiment, the orifice 5 is formed in a manner so as to be thermally isolated from the valve 2 body for reasons further disclosed herein.

In passing through orifice 5 to a low pressure location (such as the atmosphere), said gas is cooled by the J-T effect. However, due to the low thermal conductivity characteristics of the material of construction of the flow restrictor orifice assembly 4, and its configuration, which isolates orifice 5 from the outlet valve, the outlet valve 2 remains at essentially the same temperature and does not cool by conduction the inner surfaces of sample cavity 6.

Therefore condensation of heavy components of said sample gas from a final filling step, contacting the inner surfaces of outlet valve 2 and internal cavity 6, does not occur and the captured sample gas composition is not distorted. A form of said sample gas composition distortion results when heavy components condensed during the purging cycle remain in the sample cavity 6 which in turn become part of the captured gas sample and become vaporized during the required heating of gas sample cylinder 1 during the preparation for analysis of the sample gas. The present invention prevents this contamination from occurring.

Variations of the "Integral Flow Restrictor Valve"

Other flow restrictor types may be integrated into the outlet valve 2 to produce similar results. An example is flow restrictor assembly 7 in which the flow restriction element is a sintered material 8 instead of an orifice.

Another variation of outlet valve 2 design is the use of various types of valves such as a needle and ball valves. In the case of a ball valve, the flow restrictor assembly 4 or flow restrictor assembly 7 can be integrated into the "ball" of the ball valve. Like the restrictor assembly discussed above, a material having low thermal conductivity characteristics such as plastic or the like should be used to thermally isolate the orifice or sintered material from the valve body and cylinder to prevent J-T effect cooling and the associated possibility for condensation forming.

Test Results

The efficiency of the prior art method of utilizing an extension tube 11 with restrictor 13, as required by GPA standard 2166 was compared to efficiency of the aforementioned integrated restrictor outlet valve 2. The test were conducted utilizing two 300 cc constant volume sample cylinders each equipped with identical inlet and outlet valves. The prior art cylinder's outlet valve was outfitted with a 36 inch extension tube with a 0.060 inch diameter orifice at its outlet end. The second cylinder's outlet valve was outfitted with a Nylon plastic orifice assembly integrated into the outlet valve outlet port, said orifice being of a 0.060 inch diameter.

Nitrogen at 850 PSIG was utilized to perform three purge cycles on each cylinder using the GPA standard 2166 method of purge and fill. The results were that the temperature of the gas sample cylinder outlet valve body of the cylinder equipped with an extension tube and orifice was cooled 15.5 degrees F. below its initial temperature after the three purge cycles were completed. By comparison the second cylinder utilizing the present invention consisting of an outlet valve with integral flow restrictor experienced only a 4.1 degree F. reduction of its outlet valve body temperature after three purge cycles.

Preferably the outlet valve $C_v$ characteristic is large relative to the orifice $C_v$ characteristic so as to facilitate essentially all of the gas pressure drop taking place across said orifice and therefore essentially all of the J-T effect cooling taking place at said orifice. Due to the low thermal conductivity construction of said orifice an insignificant amount of cooling takes place upstream of the valve mechanism. Test have shown that the integral orifice outlet valve having a large $C_v$ characteristic is more efficient then the typical sample cylinder outlet valve and extension tube and/or flow restrictor combination.

The conclusion is that not only is the present invention easier to utilize, and more certain to be utilized by measurement technicians but actually substantially more efficient than prior art.

The invention embodiments herein described are done in detail for exemplary purposes only, and may be subject to many different variations in design, structure, application, and operation methodology. Thus, the detailed disclosures therein, should be interpreted in an illustrative, exemplary manner, not in a limited sense.

Yet another variation is the use of a low thermal conduction material for construction of outlet valve 2.

A second embodiment of the present invention contemplates a flow restricting orifice constructed of a high thermal conduction material, such as a metal, having a low thermal conduction material, such as a plastic, forming a thermal barrier between said orifice and positioned downstream of said valve's valving mechanism.

In addition to the restrictor being formed of low thermal conductivity material, it is noted that the valve body could be formed of low thermal conductivity material such as polymeric material, to isolate J-T effect cooling at the orifice area and prevent condensation within the valve body or sample cylinder.

A third embodiment of the present invention contemplates the thermal flow restriction of said first and second embodiments to be of a sintered material as opposed to an orifice. The sintered material could comprise, for example, a fine mesh stainless steel screen with a teflon liner for low thermal conductivity.

It is therefore an object of the present invention to provide a sample cylinder outlet valve which essentially eliminates J-T effect cooling of said outlet valve due to depressurization of said sample cylinder during a purging operation.

It is another object of the present invention to provide a means for essential elimination of the J-T effect cooling of a sample cylinder outlet valve which requires no action from the technician performing the spot sampling therefore assuring that spot sampling method is executed properly. Assurance comes from the fact that the required flow restriction is integrated into the cylinder outlet valve and therefore must be utilized.

Exemplary Specification

Exemplary Sample Cylinder: Whitey brand DOT-3E 1800 304L-HDF3-300 cc

Exemplary Needle Valve: Whitey SS-IRM4 Cv=0.37

Exemplary Orifice diameter: 0.060" (an orifice measuring 0.020" was also tested).

Exemplary gas: Nitrogen

Tests were conducted at pressures of 850, 1800 PSIG and 100 PSIG

What I claim is:

1. A method of spot sampling of a gas, comprising the steps of:
   a) providing a sample cylinder having first and second ends, said first end engaged to pressurized container having gas therein;
   b) providing a valve formed of a body having a conduit formed therethrough, said conduit containing a restrictor element having an orifice;
   c) affixing said valve to said second end of said sample cylinder
   d) allowing the passage of gas from said pressurized container into said sample cylinder;
   e) opening said valve to allow the passage of gas from said sample cylinder through said valve conduit;
   f) utilizing said restrictor element to block passage of said gas through said valve except by way of said orifice formed therethrough;
   g) allowing said gas to pass through said orifice, in such a manner as to decrease the flow rate of fluid therethrough, resulting in Joules-Thomson effect cooling; while
   h) utilizing material having low thermal conductivity associated with said restrictor to isolate said Joules-Thomson effect so as to prevent condensation in said valve body conduit and said sample cylinder.

2. The method of claim 1, wherein in step "b" said restrictor element comprises material having a low thermal conductivity situated between said orifice and said valve body and wherein in step "h" said restrictor element thermally isolates said orifice.

3. The method of claim 2, wherein said low thermal conductivity material coaxially envelopes said orifice formed in said restrictor.

4. The method of claim 3, wherein in step "b" said valve has first and second ends, said first end formed to engage said sample cylinder, said second end having said restrictor element formed therein.

5. The method of claim 4, wherein said restrictor element is integral to said valve.

6. The method of claim 5, wherein said restrictor element is situated downstream from said valve element.

7. The method of claim 4, wherein said restrictor element is formed of polymeric material.

8. The method of claim 7, wherein said polymeric material comprises thermoplastic.

9. The method of claim 8, wherein said polymeric material comprises PTFE.

10. The method of claim 8, wherein said polymeric material comprises PCTFE.

11. The method of claim 8, wherein said polymeric comprises NYLON.

12. The method of claim 5, wherein in step "b" said valve comprises a needle valve.

13. The method of claim 5, wherein in step "b" said valve comprises a ball valve.

14. The method of claim 13, wherein said ball valve comprises a ball, and wherein said flow restrictor element is situated in said ball.

15. The method of claim 14 wherein in step "b" said restrictor element contains sintered material to decrease the flow of gas therethrough, and wherein in step "g" said sintered material is used to decrease the flow rate of gas therethrough.

16. The method of claim 14, wherein in step "b" said orifice in said restrictor element has a diameter less than the diameter of said conduit in said valve body, providing a decreased diameter, and wherein in step "g" said decreased diameter of said orifice is used to decrease the flow of gas therethrough.

17. The method of claim 4, wherein in step "b" said restrictor element contains sintered material to decrease the flow of gas therethrough, and wherein in step "g" said sintered material is used to decrease the flow rate of gas therethrough.

18. The method of claim 4, wherein in step "b" said orifice in said restrictor element has a diameter less than the diameter of said conduit in said valve body, providing a decreased diameter, and wherein in step "g" said decreased diameter of said orifice is used to decrease the flow of gas therethrough.

19. The method of claim 3, wherein in step "b" said conduit formed in said valve body has a Cv greater than the Cv of said orifice formed in said restrictor so as to provide a flow differential, and wherein in step "h" there is provided the additional step of utilizing said flow differential so as to facilitate a pressure drop as said fluid passes through said orifice, so as to isolate said Joules-Thomson effect at said orifice.

20. The method of isolating Joules-Thomson effect cooling at an orifice, comprising the step of coaxially enveloping said orifice in material having low thermal conductivity.

21. The method of claim 20, wherein said low thermal conductivity material is polymeric.

22. The method of isolating Joules-Thomson effect cooling at an orifice, comprising the steps of
   a. providing a fluid sample cylinder having an outlet;
   b. providing a fluid flow rate limiting orifice in fluid communication with said outlet;
   c. positioning a thermal barrier in series between said outlet and said fluid flow rate limiting orifice;
   d. flowing fluid from said fluid sample cylinder through said fluid flow rate limiting orifice so as to facilitate a Joules-Thomson cooling effect; and
   e. utilizing said thermal barrier to isolate said Joules-Thomson cooling effect.

23. The method of claim 22, wherein said thermal barrier in step "c" comprises polymeric material.

24. The method of claim 23, wherein in step "d" said fluid flows through a passage formed in said thermal barrier.

25. The method of isolating Joules-Thomson effect cooling at an orifice, comprising the steps of a. providing a fluid sample cylinder having an outlet;
b. providing a flow restrictor comprising a passageway having sintered material situated therein in fluid communication with said outlet;
c. positioning a thermal barrier in series between said outlet and said flow restrictor;
d. flowing fluid from said fluid sample cylinder through said flow restrictor so as to facilitate a Joules-Thomson cooling effect; and
e. utilizing said thermal barrier to isolate said Joules-Thomson cooling effect.

26. The method of claim 25, wherein said thermal barrier in step "c" comprises polymeric material.

27. The method of claim 26, wherein in step "d" said fluid flows through a passage formed in said thermal barrier.

* * * * *